US008262700B2

(12) United States Patent
Cho et al.

(10) Patent No.: US 8,262,700 B2
(45) Date of Patent: Sep. 11, 2012

(54) TRANSVERSE SPINAL LINKING DEVICE AND SYSTEM (75) Inventors: Paul Cho, Colleyville, TX (US); Gregory Hoffman, Fort Wayne, IN (US); Hervé Chataigner, Boussieres (FR)

(73) Assignee: LDR Medical, Rosières Près Troyes (FR)

( * ) Notice: Subject to any disclaimer, the term of this patent is extended or adjusted under 35 U.S.C. 154(b) by 731 days.

(21) Appl. No.: 12/172,074

(22) Filed: Jul. 11, 2008

(65) Prior Publication Data
US 2009/0099604 A1    Apr. 16, 2009

(30) Foreign Application Priority Data
Jul. 12, 2007 (FR) ..................... 07 05066

(51) Int. Cl.
*A61B 17/70* (2006.01)
(52) U.S. Cl. .................. 606/250; 606/277; 606/278
(58) Field of Classification Search .................. 606/250, 606/278, 277, 264, 246, 262, 257, 253, 279, 606/260, 268, 251, 252, 276
See application file for complete search history.

(56) References Cited

U.S. PATENT DOCUMENTS

| 5,702,393 | A  | * | 12/1997 | Pfaifer ........................ 606/328 |
| 6,368,320 | B1 | * | 4/2002  | Le Couedic et al. ......... 606/250 |
| 7,037,340 | B2 |   | 5/2006  | Gau |
| 7,056,344 | B2 |   | 6/2006  | Huppert et al. |
| 7,291,170 | B2 |   | 11/2007 | Huppert |
| 7,326,250 | B2 |   | 2/2008  | Beaurain et al. |
| 7,494,508 | B2 |   | 2/2009  | Zeegers |
| 7,507,248 | B2 |   | 3/2009  | Beaurain et al. |
| 7,594,931 | B2 |   | 9/2009  | Louis et al. |
| 7,632,282 | B2 |   | 12/2009 | Dinville |
| 7,666,210 | B2 | * | 2/2010  | Franck et al. ................. 606/250 |
| 7,682,396 | B2 |   | 3/2010  | Beaurain et al. |
| 7,695,516 | B2 |   | 4/2010  | Zeegers |
| 7,695,518 | B2 |   | 4/2010  | Gau |

(Continued)

FOREIGN PATENT DOCUMENTS
EP    0793947    9/1997
(Continued)

OTHER PUBLICATIONS
U.S. Appl. No. 10/492,753, filed Aug. 9, 2004, Progressive approach osteosynthesis device and preassembly method.
(Continued)

*Primary Examiner* — Pedro Philogene
(74) *Attorney, Agent, or Firm* — Denko Coburn & Lauff LLP (57) ABSTRACT

A transverse spinal linking device links at least one spinal osteosynthesis bar to a transverse bar. The device may include a first part that has a vertical axis and a first jaw, a second part that has a second jaw, and a clamping resource. The first part may include a sliding surface, which may be inclined in relation to the vertical axis, and which may mate with at least one sliding surface of the second part. The sliding surfaces may be configured so that the descent of the second part results in an approach of the jaws, with the clamping action of the clamping resource causing the fixing and/or the locking of the device on the osteosynthesis bar and the fixing and/or the locking of the transverse bar.

20 Claims, 11 Drawing Sheets

U.S. PATENT DOCUMENTS

| | | | |
|---|---|---|---|
| 7,842,088 B2 | 11/2010 | Rashbaum et al. | |
| 8,002,835 B2 | 8/2011 | Zeegers | |
| 8,147,556 B2 | 4/2012 | Louis et al. | |
| 8,162,988 B2 | 4/2012 | Delecrin et al. | |
| 2006/0064091 A1 | 3/2006 | Ludwig et al. | |
| 2007/0083201 A1 | 4/2007 | Jones et al. | |

FOREIGN PATENT DOCUMENTS

| | | | | |
|---|---|---|---|---|
| EP | 0813845 | * | 12/1997 | ................ 606/250 |
| FR | 2732887 | * | 10/1996 | ................ 606/250 |
| FR | 2771918 | | 6/1999 | |
| FR | 2861981 | | 5/2005 | |
| WO | WO03068087 | | 8/2003 | |
| WO | WO2009007838 | | 1/2009 | |

OTHER PUBLICATIONS

U.S. Appl. No. 10/498,234, filed Dec. 7, 2004, Implant for Osseous Anchoring with Polyaxial Head.

U.S. Appl. No. 10/570,080, filed Jun. 9, 2006, Osseous anchoring implant with a polyaxial head and method for installing the implant.

U.S. Appl. No. 10/575,065, filed Apr. 7, 2006, Device and method for sectioning a vertebral lamina.

U.S. Appl. No. 11/051,710, filed Feb. 4, 2005, Intervertebral Disc Prosthesis.

U.S. Appl. No. 11/362,253, filed Feb. 24, 2006, Intervertebral Disc Prosthesis and Instrumentation for Insertion of the Prosthesis Between the Vertebrae.

U.S. Appl. No. 11/378,165, filed Mar. 17, 2006, Transforanimal intersomatic cage for an intervertebral fusion graft and an instrument for implanting the cage.

U.S. Appl. No. 11/676,237, filed Feb. 16, 2007, Intervertebral disc prosthesis insertion assemblies.

U.S. Appl. No. 11/767,386, filed Jun. 22, 2007, Intersomatic cage with unified grafts.

U.S. Appl. No. 11/874,144, filed Oct. 17, 2007, Modular intervertebral prosthesis.

U.S. Appl. No. 11/958,285, filed Dec. 17, 2007, Vertebral Support Device.

U.S. Appl. No. 12/025,677, filed Feb. 4, 2008, Intervertebral disc prosthesis, surgical methods, and fitting tools.

U.S. Appl. No. 12/134,884, filed Jun. 6, 2008, Intersomatic cage, intervertebral prosthesis, anchoring device and implantation instruments.

U.S. Appl. No. 12/172,074, filed Jul. 11, 2008, Transverse spinal linking device and system.

U.S. Appl. No. 12/279,664, filed Apr. 22, 2009, Transforaminal intersomatic cage for an intervertebral fusion graft and an instrument for implanting the cage.

U.S. Appl. No. 12/360,050, filed Jan. 26, 2009, Intervertebral Disc Prosthesis.

U.S. Appl. No. 12/409,327, filed Mar. 23, 2009, Spinal Osteosynthesis Device and Preparation Method.

U.S. Appl. No. 12/424,364, filed Apr. 15, 2009, Intervertebral Disk Prosthesis.

U.S. Appl. No. 12/435,955, filed May 5, 2009, Instrumentation and Methods for Inserting an Intervertebral Disc Prosthesis.

U.S. Appl. No. 12/527,373, filed Aug. 14, 2009, Intervertebral disc prosthesis insertion assemblies.

U.S. Appl. No. 12/562,704, filed Sep. 18, 2009, Implant for Osseous Anchoring with Polyaxial Head.

U.S. Appl. No. 12/955,898, filed Nov. 29, 2010, Intervertebral Disc Prosthesis.

U.S. Appl. No. 13/158,761, filed Jun. 13, 2011, Instruments and Methods for Removing Fixation Devices from Intervertebral Implants.

U.S. Appl. No. 13/215,123, filed Aug. 22, 2011, Intervertebral Disc Prosthesis.

U.S. Appl. No. 13/369,650, filed Feb. 9, 2012, Interspinous Implant and Implantation Instrument.

U.S. Appl. No. 13/438,352, filed Apr. 3, 2012, Vertebral Cage Device With Modular Fixation.

U.S. Appl. No. 13/454,927, filed Apr. 24, 2012, Plate for osteosynthesis device and method of preassembling such device.

World Intellectual Property Organization; International Preliminary Report on Patentability for PCT Pub'n No. WO2009007838; Aug. 14.

World Intellectual Property Organization; International Search Report for PCT Pub'n No. WO2009007838; Feb. 13.

World Intellectual Property Organization; Written Opinon of the International Searching Authority for PCT Pub'n No. WO2009007838; Feb. 13.

European Patent Office; Prosecution History for EP App'n. No. 20080826187; Jul. 11, 2008; EPO; Munich, Germany; all pages.

* cited by examiner

TRANSVERSE SPINAL LINKING DEVICE AND SYSTEM

CROSS-REFERENCE TO RELATED APPLICATIONS

This application claims priority under 35 U.S.C. §119 to French Patent Application No. 07 05066, filed in FRANCE on Jul. 12, 2007, which is incorporated herein by reference.

BACKGROUND

This present invention concerns the area of spinal implants in general and in particular osteosynthesis devices, vertebral support devices, and transverse spinal linking devices. Transverse spinal linking devices provide a transverse spacing link between two spinal osteosynthesis bars stabilizing the vertebral column and/or correcting deformations of the vertebral column. Various embodiments of the present invention provide a device that links at least one spinal osteosynthesis bar and a transverse bar. The spinal osteosynthesis bars are intended to adapt to the physiological or pathological curvatures of the vertebral column, and to stabilize the latter and/or correct its curvature defects. These spinal osteosynthesis bars are fixed along the vertebral column by means of bony anchoring resources such as pedicle screws or any other type of fixing means. Often, to facilitate correct retention of the osteosynthesis bars and to allow a good reduction and/or a good setting action, these spinal osteosynthesis bars are connected to each other at one or more points by means of transverse bars. This transverse spacing enhances the stability of the fitting and/or corrective effect (in distraction or in compression).

One problem in the area of transverse spinal linking devices concerns the fitting of these devices to fix the transverse bar to the spinal osteosynthesis bars. In fact, the osteosynthesis bars are fixed along the vertebral column, and the bulk on either side of these bars renders difficult the implantation of the transverse bars and of the transverse spinal linking devices. In fact, the implantation of the transverse spinal linking devices is often difficult because of their small size, and of their structure, which is often complicated to assemble and to mount on the osteosynthesis bars, and because of the frequent necessity to clear the surroundings of the osteosynthesis bar (possibly with an avivement or stripping of the articular processes or a resection of vertebral material).

From previous designs, in particular from patent application WO 03/068087A1 or from patent EP 0793947B1, one is familiar with transverse spinal linking devices with reduced bulk that can be installed on the osteosynthesis bar from the top (by a posterior approach in relation to the vertebral column). These devices of previous design can be mounted on osteosynthesis bars posterior to the vertebral column, using a posterior approach, and allow fixing onto the bar possibly without touching the anterior face of the bar (the side facing the vertebral column). These devices are composed of two jaws that are hinged on an axis located either between the two jaws or off-centre on one of the jaws (which is then fixed). These two jaws are used to grip the bar and to fix the device, which includes a head with a conduit perpendicular to the axis of the spinal osteosynthesis bar. A clamping resource may project into this conduit and to fix the transverse bar while also inducing the closure of the jaws. This closure of the jaws during the clamping of the bar by the clamping resource is achieved by means of the fact that the bar presses onto an edge of at least one of the jaws. These devices have the drawbacks, firstly, of being expensive and relatively complex, requiring an assembly that is complicated and sometimes not very stable, and secondly that the bar is locked between an edge of at least one of the jaws and the clamping resource, which may impose large stresses on the bar and embrittle the bar. These devices have another drawback due to the fact that the jaws tend to close spontaneously even when the clamping resource do not press the bar onto the edge of one of the jaws, which renders difficult the implantation of the devices on the osteosynthesis bar. These devices sometimes correct the latter drawback by means of the presence of stop elements that limit the closure of the two jaws, but this solution adds an extra element, and therefore increases the complexity of these devices.

In this context, it is useful to propose a transverse spinal linking device having a simpler design and a structure configured to ameliorate one or more of the problems presented above, which may allow a fixing of the bar without making the latter fragile, and whose jaws do not tend to close completely before the insertion of the devices on the osteosynthesis bar.

SUMMARY

Various embodiments of this present invention may overcome certain drawbacks of previous designs, for example by having a relatively simple design, by being relatively easy to assemble and/or to implant, by avoiding or reducing embrittlement of different elements in the assembling process by avoiding imposing large stresses on these elements, and/or by reducing the bulk of various elements.

Accordingly, various embodiments of this present invention provide a spinal stabilization system that may include a transverse link device of simple design, may be easy to assemble and/or implant, may avoid or reduce embrittlement of different elements in the assembling process (for example by avoiding imposing large stresses on various elements), and/or may have various elements with reduced bulk.

BRIEF DESCRIPTION OF THE SEVERAL VIEWS OF THE DRAWING

Other particular features and advantages of various embodiments of this present invention will appear more clearly on reading the description that follows, with reference to the appended drawings, in which:

FIGS. 5B and 5D represent detail of the area indicated respectively by reference 5B of FIG. 5A and reference 5D of FIG. 5C, FIGS. 6A and 6B represent front views of one embodiment of a transverse spinal linking device, respectively before and after fixing onto an osteosynthesis bar, the clamping axis (AS) of the clamping resource in this embodiment being aligned with the osteosynthesis bar.

DETAILED DESCRIPTION OF VARIOUS EMBODIMENTS

This present invention concerns a transverse spinal linking device (1), for attaching at least one spinal osteosynthesis bar (2) with a transverse bar (3). This type of device is generally used to connect two osteosynthesis bars to each other by means of at least one transverse bar. A spinal stabilization system may comprise a device (1), one or more transverse bars (3), and one or more osteosynthesis bars (2). Such a system may be called, by way of illustration, a "transverse spinal linking system," for example referring to embodiments configured to provide a transverse link between osteosynthesis devices or vertebral support devices, such as those described, respectively, in application FR 2 859 095 (and WO2005/020829) and in application FR 06 11198 (and U.S. Ser. No. 11/958,285), filed by the applicant, for example. These applications respectively describe examples of osteosynthesis devices and vertebral support devices on which various embodiments of this present invention may be used, although various embodiments may be used with other types of osteosynthesis devices or vertebral support devices. The invention therefore also concerns a transverse spinal linking system that comprises a device according to one of the embodiments presented here or to a similar variant. Since the different elements of such a system are intended to be implanted in patients, they will generally be implemented in a material that has been approved for implantation.

Figure 1A:
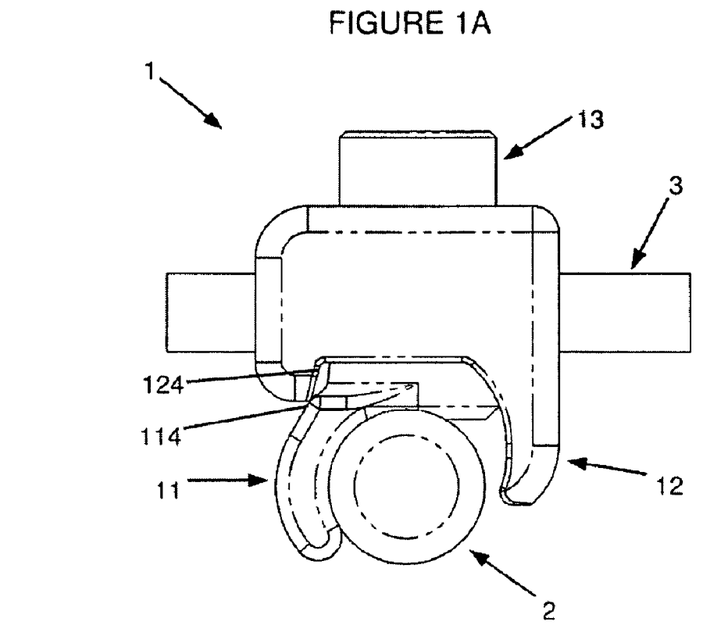
FIGS. 1A and 1B represent front views of one method of implementation of a transverse spinal linking system embodiment, respectively before and after fixing onto an osteosynthesis bar, FIGS. 2A and 2B respectively represent views in perspective of a system in exploded view and assembled, according to a transverse spinal linking system embodiment.
Figure 1B:
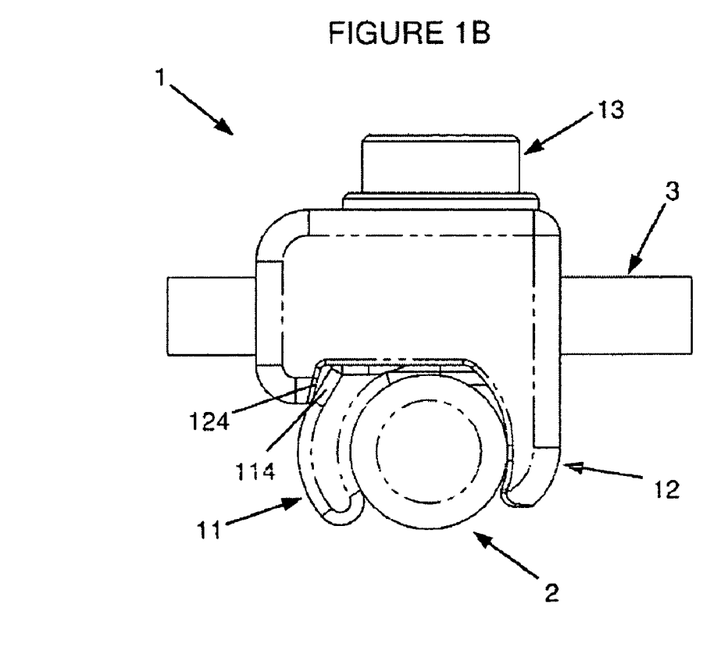
Figure 2A:
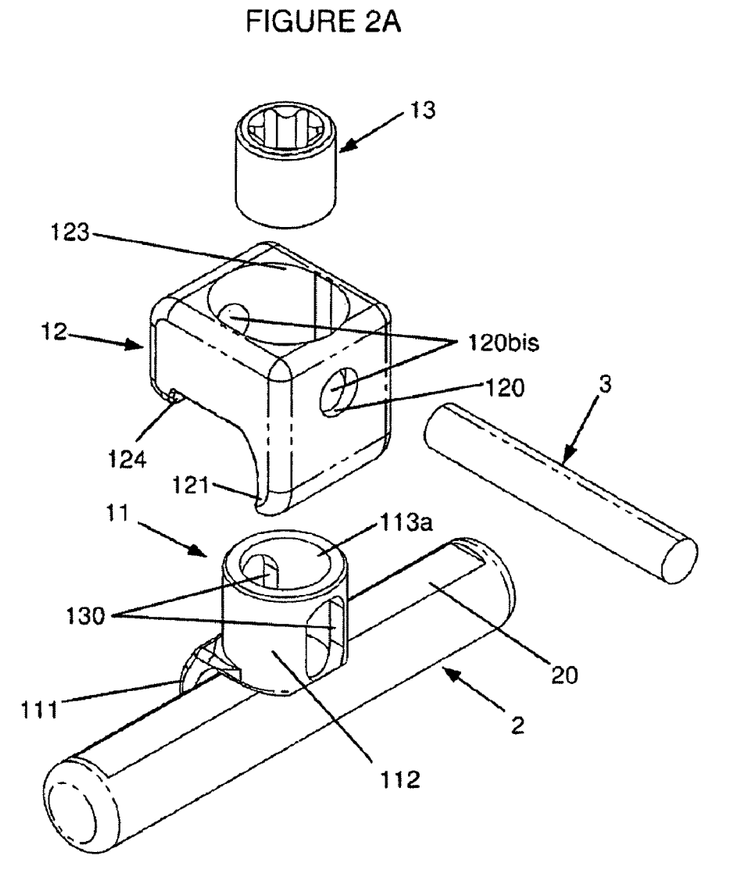
Figure 2B:
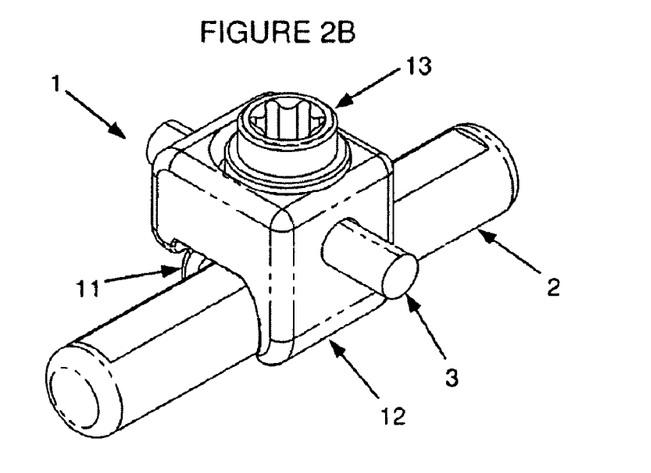

Various transverse spinal linking device embodiments (I) may include jaws (111, 121) intended to grip a spinal osteosynthesis bar (2) and a bearing surface (120) intended to support a transverse bar (3). For example, a device (1) may include a first part (11) that has a first jaw (111) and a fixing head (112) that mates with clamping resource (13) pressing onto the transverse bar (3). A device (1) may also include a second part (12) that has a second jaw (121) and a fixing body that has a passage (123) engaging or receiving the fixing head (112) of the first part (11), along an axis that is substantially orientated in the direction of the osteosynthesis bar (2). Here, this axis is called the vertical axis and is represented as being substantially vertical in figures of the device (1). However, what is meant here by the term "vertical axis" is the axis along which the second part (12) and/or the clamping resource (13) engage the first part (11), but it will be apparent to the professional, on reading this present description, that this so-called vertical axis may be orientated differently, and is not necessarily vertical in any absolute or sense. It should also be noted here that in operation, when the device is fixed onto the osteosynthesis bars (2), this axis generally may be substantially perpendicular to the longitudinal axis of the vertebral column, and therefore generally may be substantially horizontal if the patient carrying the device is upright. The terminology used, therefore, is to be interpreted only as a guide when referring to the device such as represented in the illustrative drawings, like FIG. 1A for example. However, during the implantation process, the patient typically is lying on his stomach, and the device will be positioned onto the osteosynthesis bar (2) from the top downwards, which is then vertical in fact. This so-called vertical axis will preferably be orientated substantially in the direction of the osteosynthesis bar (2) to be fixed by the device (1), and various embodiments of the invention allow the device to be fixed along the osteosynthesis bar with a certain angulation in relation to the latter. Likewise, when other structures are said to be vertical in this present description, such orientation generally is with reference to a direction from the osteosynthesis bar to the spinal column.

In various embodiments, the passage (123) in the second part (12) by which the latter engages the fixing head (112) of the first part (11) may have larger dimensions than the fixing head (112), at least along an approach axis of the jaws (for example, perpendicular to the orientation of the osteosynthesis bar). Thus, for example, this passage (123) may be of elongated or oblong or ovoid shape, or other shape providing play or some freedom of movement of the second part (12) in relation to the first part (11), at least along an approach axis of the jaws (111, 121). However, this passage (123) may also be larger in other directions, in addition to that of the approach of the jaws (111, 121), and may therefore have any shape as long as it is designed to engage or receive the fixing head (112). In one method of implementation, shown in FIGS. 2A, 2B and 3A to 3D, the fixing head (112) of the first part (11) is of substantially cylindrical shape, and the passage (123) in the fixing body of the second part (12) is of substantially oblong or elongated shape to create transverse play of the second part (12) in relation to the first (11), along an axis of the approach of the jaws (111, 121). As explained below, this transverse play allows the approach of the jaws (111, 121) during the closure of the clamping resource (13). The particularly advantageous cylindrical shape of the fixing head (112) is only illustrative, and it will be clear to the professional that the latter may be polyhedral or have any shape. The passage (123) also may have different shapes, preferably complementary to that of the fixing head (112). This shape of the passage preferably allows the fixing body of the second part (12) to engage or receive the fixing head (112) of the first part (11), and it is not necessary for the passage (123) to have exactly the same shape as the head (112). Likewise, the fixing body of the second part (12) is represented in FIGS. 2A, 2B, 3A, and 3B as being substantially cubic, with rounded edges, but other shapes may be used.

Figure 7A:
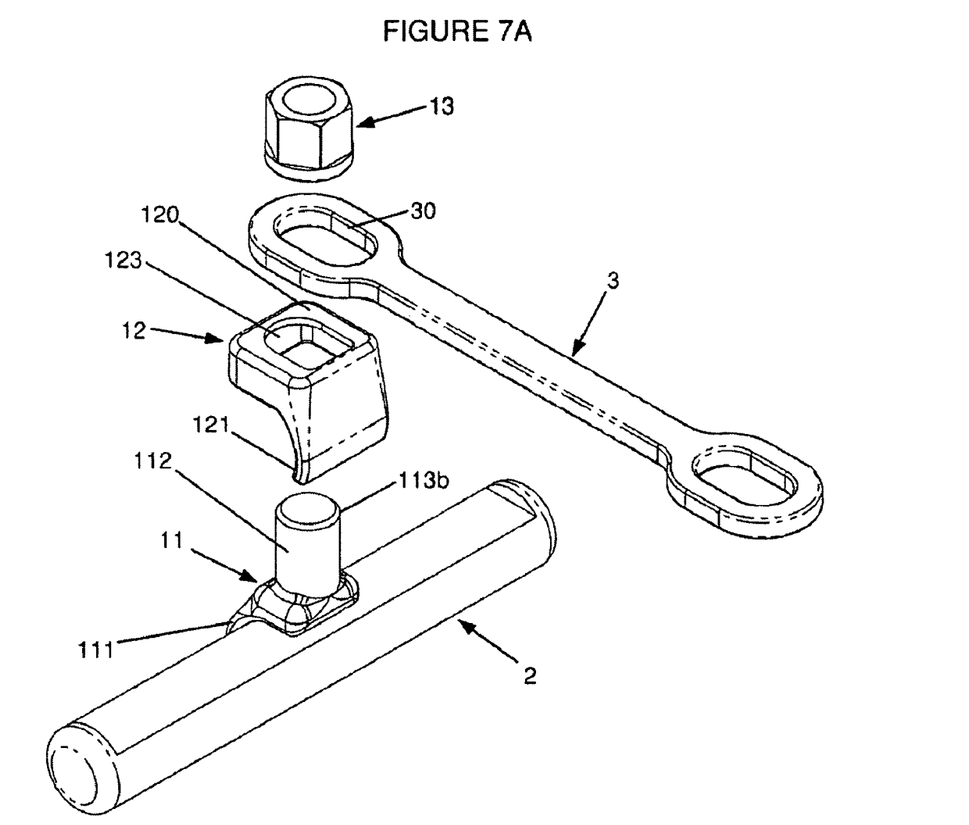
Figure 7B:
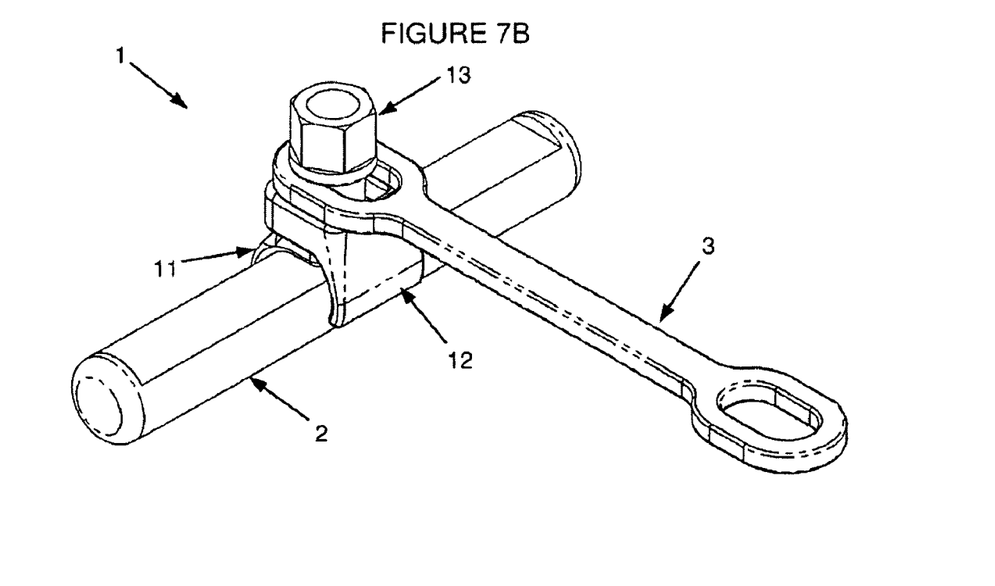
Figure 8A:
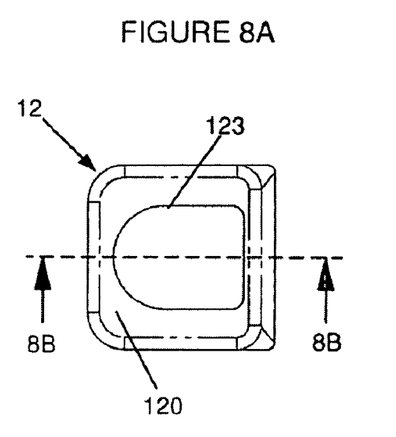
FIGS. 8A and 8C represent a view from above of a second part and a first part, respectively, of a transverse spinal linking device embodiment, and FIGS. 8B and 8D respectively represent views in section along axis 8B-8B of FIG. 8A and axis 8D-8D of FIG. 8C, FIGS. 9A and 9B respectively represent a view from above of a transverse spinal linking system embodiment, before and after locking the device, FIGS. 10A and 10C respectively represent views in section along axis 10A-10A of FIG. 9A and axis 10C-10C of FIG. 9B, respectively before and after locking the device, and FIGS. 10B and 10D respectively represent a detail of the device indicated by the area referenced 10B in FIG. 10A and by the area referenced 10D in FIG. 10C, and FIGS. 11A and 11B represent views in perspective of two transverse spinal linking system embodiments.
Figure 8B:
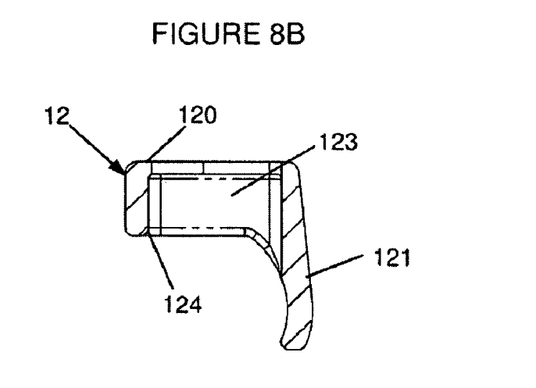
Figure 8C:
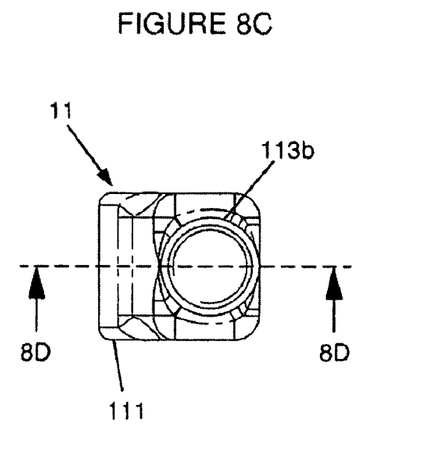
Figure 8D:
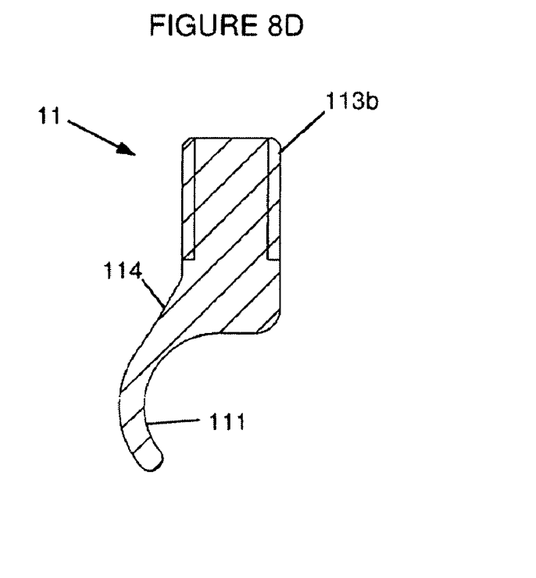
Figure 9A:
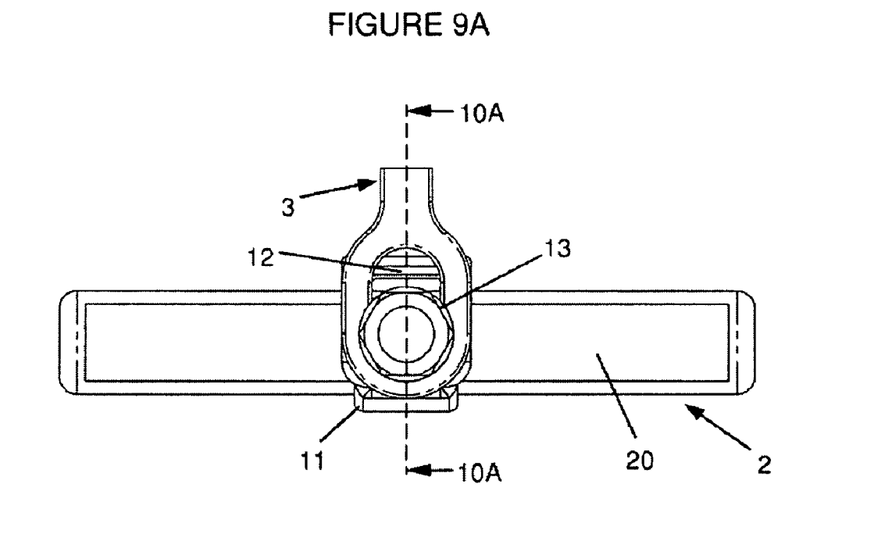
Figure 9B:
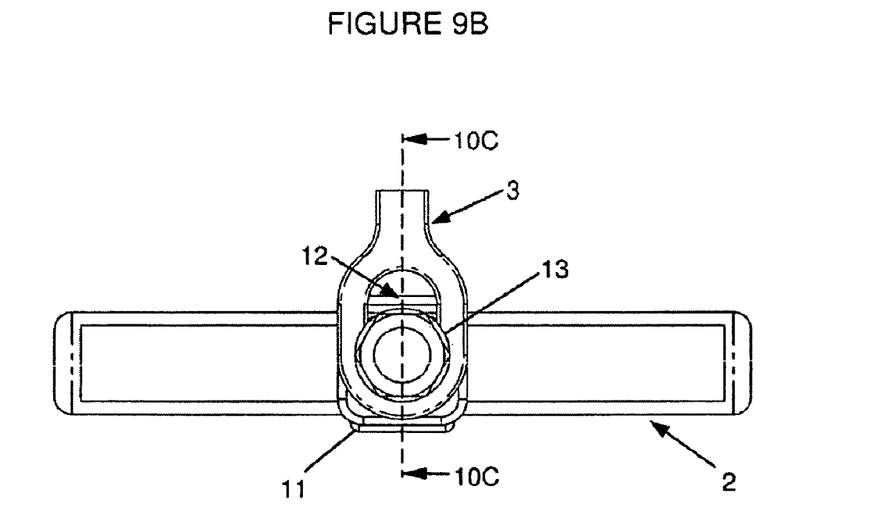
Figure 10A:
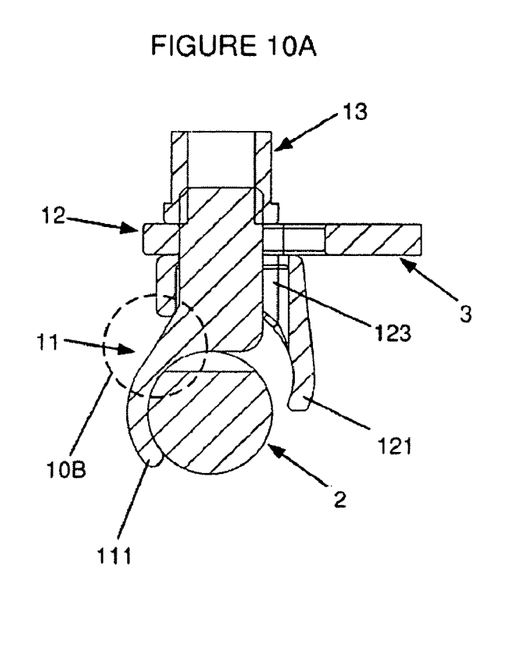
Figure 10B:
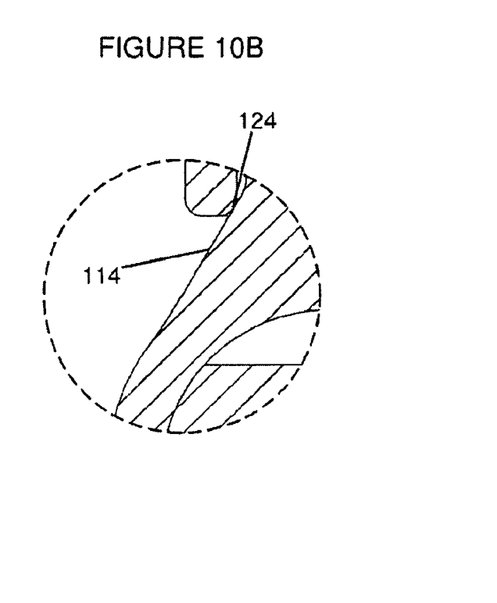
Figure 10C:
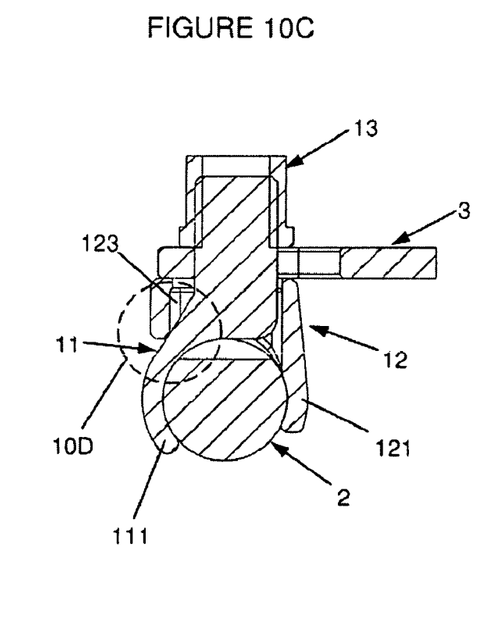
Figure 10D:
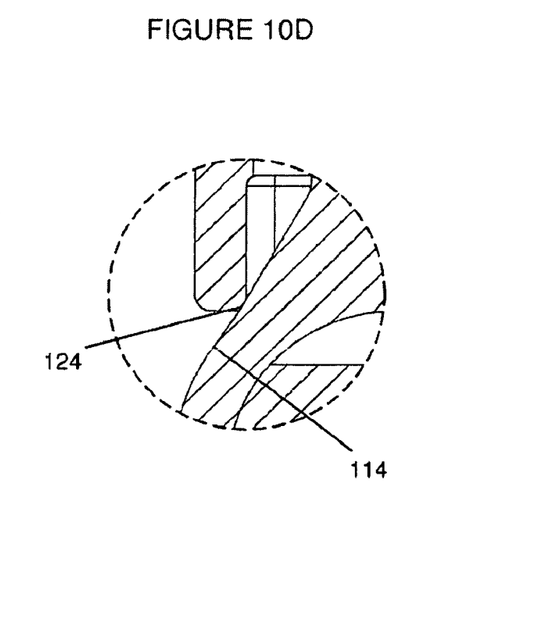
Figure 11A:
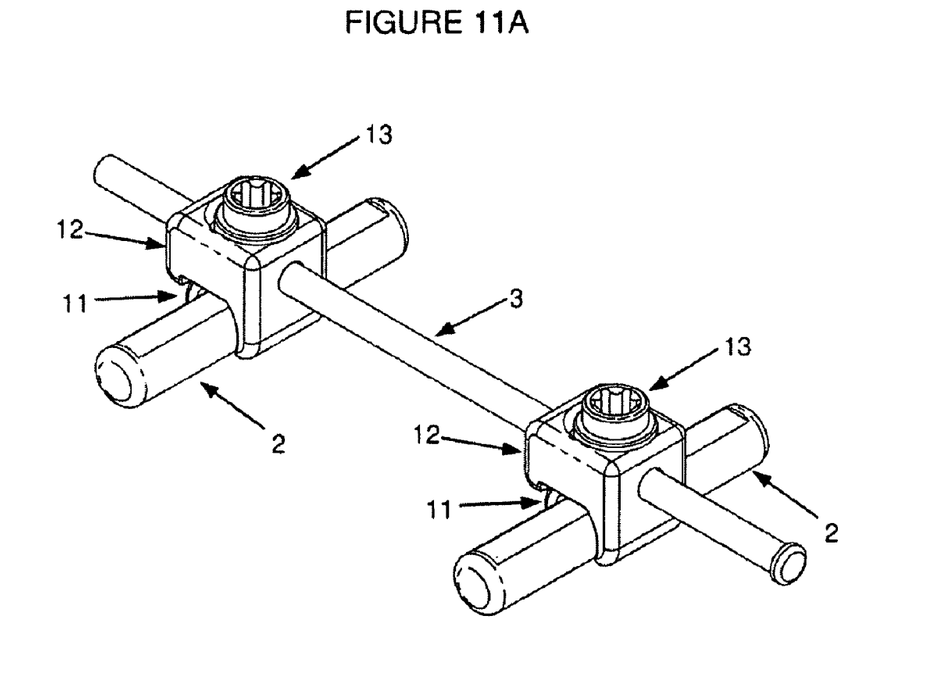
Figure 11B:
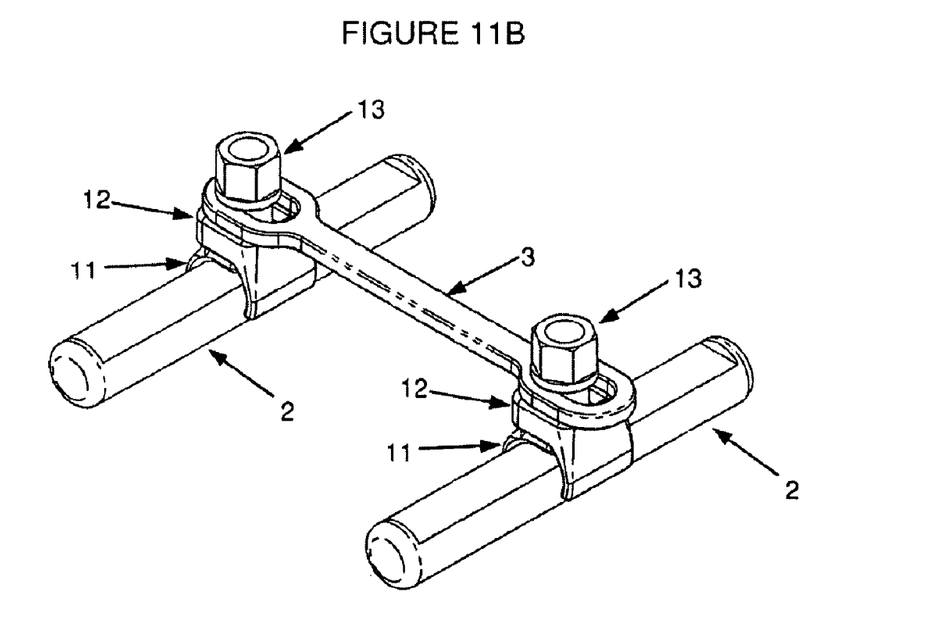

In various embodiments, the clamping resource (13) may be arranged in such a manner that its clamping action induces its descent in relation to the head (112) of the first part (11). In operation, the clamping resource thus may move the transverse bar (3) closer to at least one surface of the first part (11) and/or the second part (12). In an advantageous manner, the clamping resource (13) may press onto the bar (3), which presses onto the second part (12) and thus causes it to approach the first part (11). This descent of the clamping resource (13) causes the transverse bar (3) to bear against the bearing surface (120) of the second part (12) and the second part (12) to descend in relation to the first part (11). In addition, the first part (11) may include a sliding surface (114) inclined in relation to the vertical axis of the device (1). This sliding surface (114) and the vertical axis of the device (1) therefore form an angle. This sliding surface (114) of the first part (11) may mate with at least one sliding surface (124) of the second part (12) thus guiding the second part (12) in relation to the first part (11). Therefore by the contact between these two sliding surfaces (114, 124), the descent of the second part (12) in relation to the first part (11) results in an approach of the jaws (121, 111). Thus, during the clamping action of the clamping resource (13), the sliding surface (124) of the second part (12) slides along the inclined sliding surface (114) of the first part (11) and by means of the play allowed by passage (123) the second part (12) is moved sideways and causes the approach of the second jaw (121) in relation to the first jaw (111). The clamping action of the clamping resource (13) causes the descent of the transverse bar (3) pressing onto the second part (12), via the bearing surface (120), and the descent of the second part (12) causes the closure of the jaws (121, 111), via the sliding surfaces (114, 124). A further closure of the clamping resource (13) then causes the fixing and/or the locking of the device (1) on the osteosynthesis bar (2), trapped between the jaws, and the fixing and/or the locking of the transverse bar (3), trapped between the clamping resource (13) and the bearing surface (120). In a particularly advantageous manner, the transverse bar (3) and the bearing surface (120) cooperate by at least a portion of complementary shape. For example, FIG. 7A shows a substantially flat bearing surface (120). Thus, the forces exerted on the bar and on the bearing surface during the clamping action of the clamping resource (13) may be better absorbed by the contact surfaces, which may benefit the materials and may help preserve the integrity of the assembly.

In various embodiments, the two jaws may have shapes and dimensions configured to grip the osteosynthesis bar (2) while leaving free a substantial part of its periphery even during the fixing and/or the locking of the device (1), as shown particularly in FIGS. 1B, 5C, 6B and 10C. These particularly advantageous embodiments allow the device (1) to be placed on the osteosynthesis bars (2) without covering their anterior face (the face located alongside the vertebral column). This particular feature may facilitate the implantation of the device by reducing its size. Thus, for such embodiments the device (1) may be implanted on the bar (2) by a posterior approach, and may not require the clearance of space around the osteosynthesis bar (2) or in the vertebrae (such as the articular processes).

In various embodiments, at least one of the first (11) and second (12) parts may include a stop element limiting the approach of the two jaws (111, 121). As shown particularly in the figures, this stop element may in fact comprise simply the relative size of the passage (123) of the second part (12) in relation to the fixing head (112) of the first part (11). The lateral (or transverse) play provided by this size difference is easily limited, and such a stop function may be implemented simply by the contact of an inside edge of the passage (123) with an outside edge of the fixing head and/or contact of the sliding surface (114) of the first part (11) with the sliding surface (124) of the second part (12). In various embodiments, the stop function may be implemented in such a manner that the two jaws (111, 121) form between them, in the closest approach position, sufficient space so that a thrust exerted on the device (1) in the position bearing onto the osteosynthesis bar (2) causes the opening of the jaws (111, 121) and allows placement of the device (1) onto the osteosynthesis bar (2).

In various embodiments, the two jaws (111, 121) may be substantially symmetrical, and each may include a clamping surface acting in an opposing manner on the osteosynthesis bar (2), thus enabling them to be fitted to osteosynthesis bars (2) of different diameters. For example, the clamping surfaces may be concave, having a profile suitable for reliable securing to the osteosynthesis bar. The clamping surfaces may have a radius of curvature that is constant or not, and may thus have a single concavity or a double concavity or a triple concavity, and so on. Thus, by means of this multiple concavity option, the clamping surfaces may be particularly suitable for clamping osteosynthesis bars (2) of differing diameters.

Figure 3A:
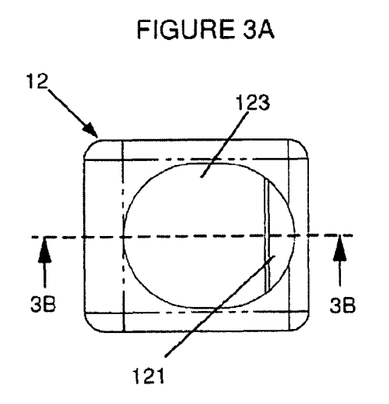
FIGS. 3A and 3C represent a view from above of a second part and a first part, respectively, of a transverse spinal linking device embodiment, and FIGS. 3B and 3D respectively represent views in section, along axis 3B-3B of FIG. 3A and axis 3D-3D of FIG. 3C, of the second and first parts of such embodiment.
Figure 3B:
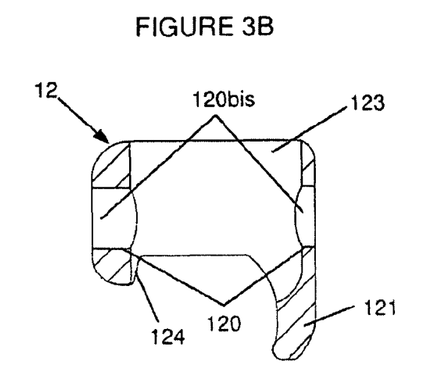
Figure 3C:
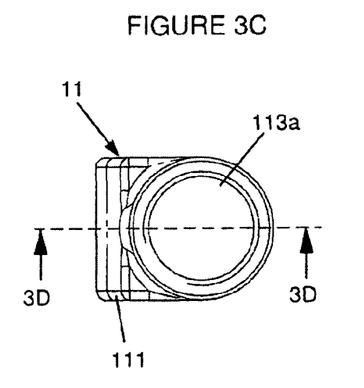
Figure 3D:
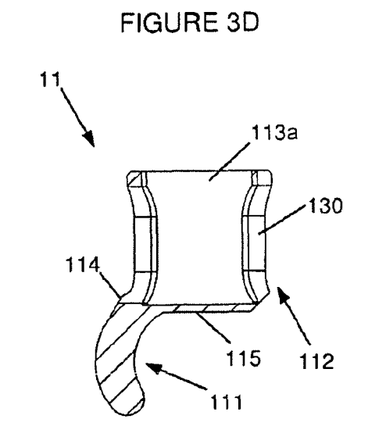
Figure 4A:
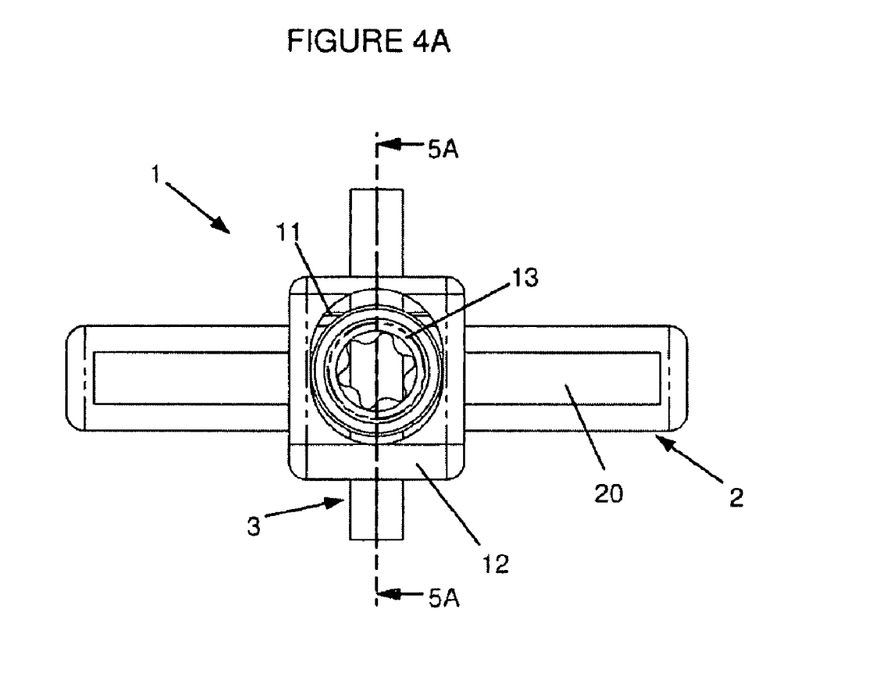
FIGS. 4A and 4B represent views from above of a transverse spinal linking system embodiment, respectively before and after locking of the device.
Figure 4B:
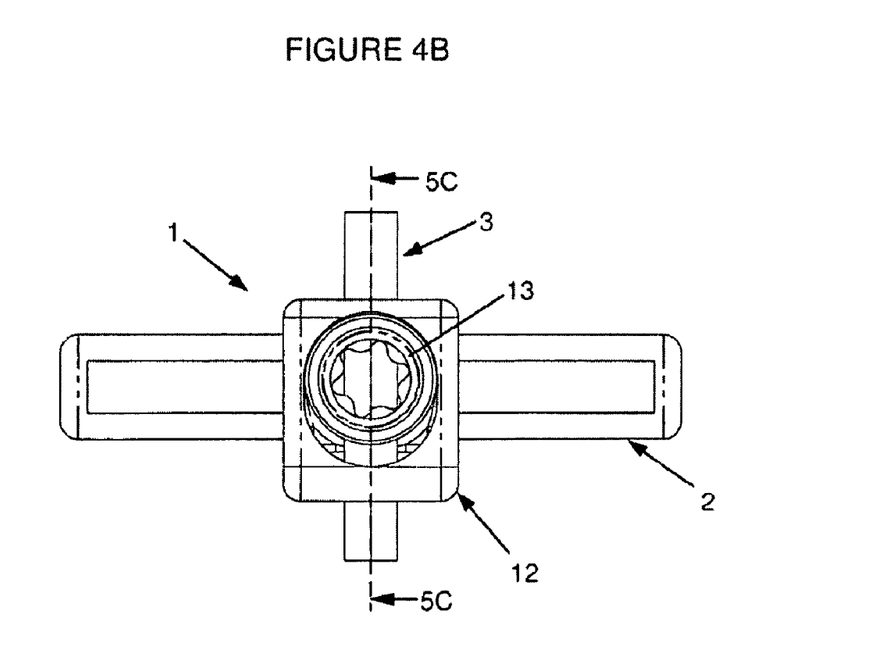
Figure 5A:
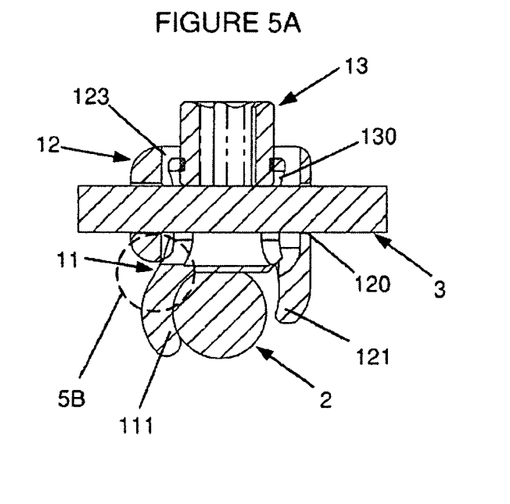
FIGS. 5A and 5C represent views in section, respectively along axis 5A-5A of FIG. 4A and axis 5C-5C of FIG. 4B, respectively before and after locking.
Figure 5B:
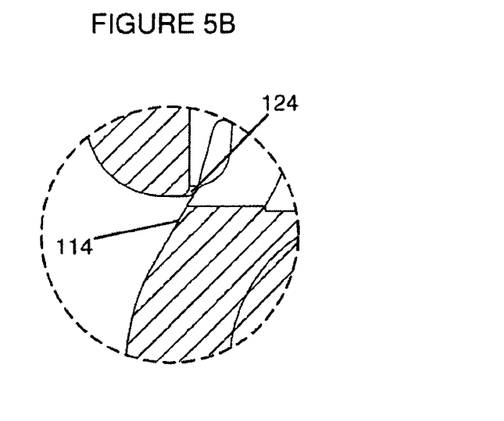
Figure 5C:
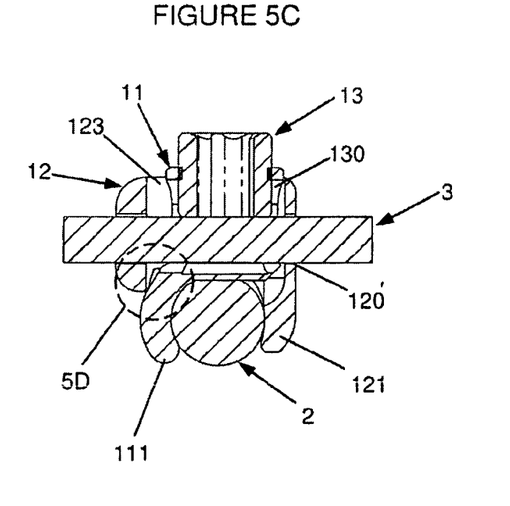
Figure 5D:
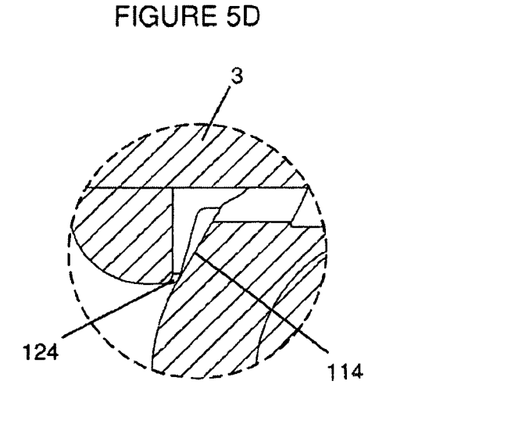

In various embodiments, an example of which is particularly visible in FIG. 3D, the first jaw (111) is extended, at its link to the fixing head (112), by a surface (115) that is complementary to a surface of the osteosynthesis bar (2), which helps stabilize the device (1) on the bar (2). For example, in FIG. 3D, this surface (115) of the first part (11) is substantially horizontal and flat, so as to mate with a flat area (20, FIG. 2A) of the bar (2). The cooperation between this flat area and this bottom flat area of the first part allows the device (1) to be positioned on the bar (2) and moveably retained before the clamping action, which allows the device (1) to be moved along the bar, for example in order to adjust its position along the vertebral column.

In various embodiments, examples of which are particularly visible in FIGS. 1 to 5, the first part (11) includes a passage (130) that is substantially oblong or elongated along the vertical axis, in order to accept the transverse bar (3) and to allow its descent during the clamping action of the clamping resource (13). In various embodiments, the second part (12) also includes a passage (120bis) configured to receive the transverse bar (3). This passage includes the bearing surface (120), by means of which the transverse bar (3) presses onto the second part (12) for the approach of the first part (11). In the example shown, this bearing surface (120) of the transverse bar (3) is formed by the bottom surface of the passage (120bis), as shown particularly in FIGS. 2A and 3B. In various embodiments, this passage (120bis) may open onto the top surface of the fixing body of the second part, in such a manner that the transverse bar (3) may be inserted into it from the top. Preferably, this passage (120bis) comprises a hole drilled through the fixing body of the second part and the transverse bar (3) is inserted into it by the side. In most of the variants, this passage will have a diameter that is slightly larger than that of the transverse bar. These passages (130) of the first part (11) and (120bis) of the second part (12) are preferably orientated substantially perpendicular to the axis of the osteosynthesis bar (2), which typically will be substantially parallel to the approach axis of the jaws (111, 121). These two passages (120bis, 130) are therefore preferably orientated so as to allow fixing of the transverse bar (3) substantially perpendicular to the osteosynthesis bar (2). In certain variants, these passages may form an angle in relation to this approach axis of the jaws (111, 121). In various embodiments, the passages (130) of the first part (11) and (120bis) of the second part (12) may have a flared profile, and/or may be substantially wider than the diameter of the transverse bar (3), in a manner to allow movement of the transverse bar (3), which may then be fixed with an orientation that is perpendicular or not to the axis of the osteosynthesis bar (2). Thus, the shapes and dimensions of the two passages (120bis, 130) are arranged so as to allow movement of the transverse bar (3) around at least one axis perpendicular to the osteosynthesis bar (2). In particular, these shapes may comprise parallelepipeds, cylinders, etc. In these embodiments, amongst other things, the fixing head (112) of the first part (11) includes a vertical conduit (113a) opening onto the passage (130) and into which the clamping resource (13) may be inserted in order to fix the transverse bar (3). This vertical conduit (113a) may then include a tapping that mates with a thread located on the periphery of at least one portion of the clamping resource (13). The clamping resource may then comprise a screw whose head includes a hexagonal hole (blind or not) or a star-shaped hole or any shape intended to mate with a tool of a known type.

In other embodiments, examples of which are particularly visible in FIGS. 6 to 10, the fixing head (112) of the first part (11) may include a stud (113b) projecting through a passage (123) of the second part (12) when the latter is disposed about the fixing head (112). The stud (113b) may be configured to receive a clamping resource (13). The passage (123), for example, may open onto a bearing surface (120), and the transverse bar (3) may include, close to at least one of its ends, a passage (30) intended to be disposed about the stud (113b). This passage (30) may comprise an eyelet at the end of the bar, that comprises a widening of the bar and an aperture, for example as shown in FIG. 7A, or slot, or comprises simply an aperture or slot in the bar. This passage (30) allows the transverse bar (3) to be disposed about the stud (113b) and pressed onto the bearing surface (120) of the second part (12). Thus, the clamping resource (13) mounted on the stud (113b) may cause the descent of the transverse bar (3) and the second part (12). In these embodiments, amongst other things, the stud (113b) may include a thread on the periphery of its top end that is intended to mate with a tapping located on at least a portion of the clamping resource (13). Thus, the clamping resource (13) may comprise a nut or any type of tapped female structure that may be screwed onto the threaded stud. In these embodiments, the shapes and dimensions of the stud (113b) and of the passage (30) of the transverse bar (3) are arranged so as to allow movement of the transverse bar (3) in relation to the rest of the device (1). The bearing surface (120) is substantially flat, and intended to mate with a substantially flat bottom surface of the transverse bar (3). In other variants, the bearing surface may be concave and the bar cylindrical, or any other possible combination of these variants.

In the embodiments presented above, when the fixing head (112) of the first part (11) includes a vertical conduit (113a) opening onto the passage (130), and into which the clamping resource (13) is inserted, the fixing head may include a thread on its periphery, intended to mate with a tapped hole in the clamping resource (13), at the centre of which a stud is intended to penetrate into the conduit (113a). This example illustrates that the embodiments presented here for the clamping resource are purely illustrative, and after appreciating this disclosure the professional will understand that other clamping resource also are within the scope of the invention. In addition, the clamping action may be achieved using structures that are different from the mating action between thread and tapping presented here.

Figure 6A:
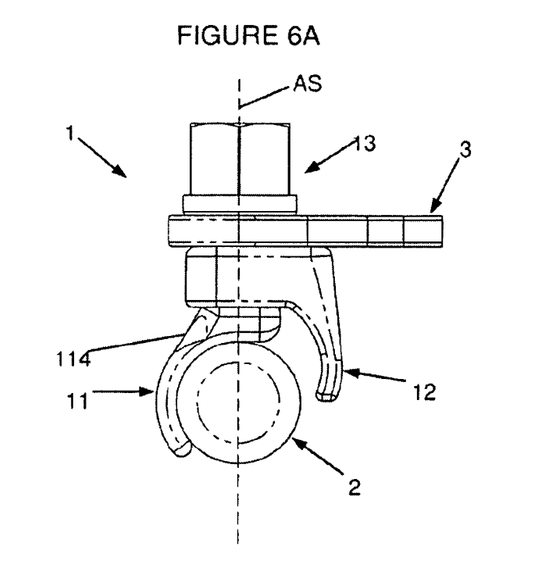
Figure 6B:
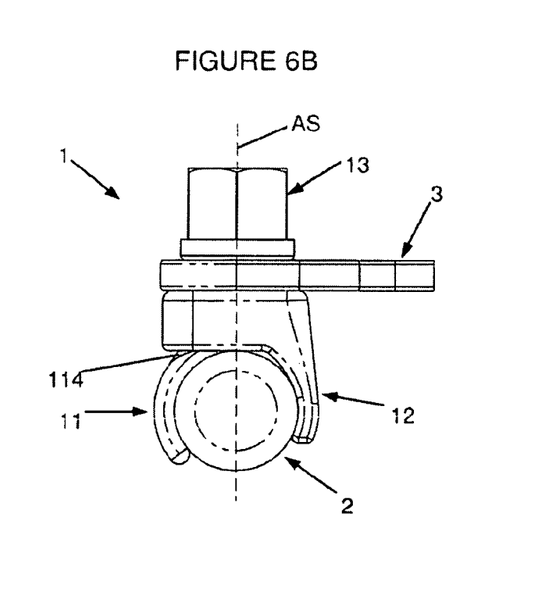
Figure 6C:
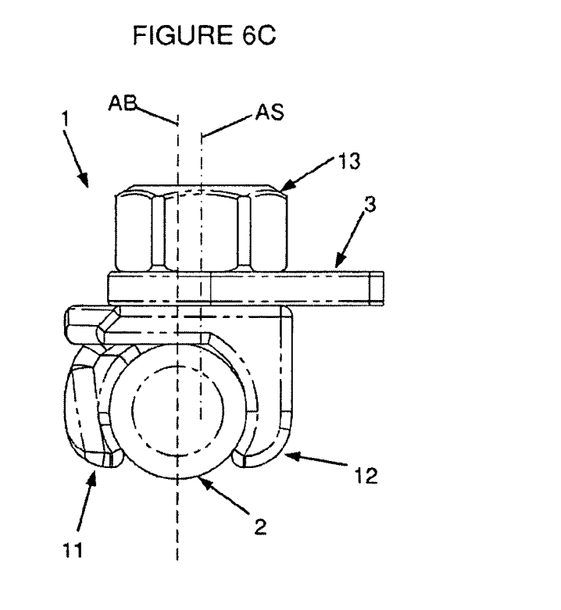
FIGS. 6C and 6D represent front views of another embodiment of a transverse spinal linking device, after fixing onto an osteosynthesis bar, the clamping axis (AS) of the clamping resource in this embodiment being offset in relation to the axis (AB) of the osteosynthesis bar, FIGS. 7A and 7B respectively represent views in perspective of a system in exploded view and of such system assembled, according to a transverse spinal linking system embodiment.
Figure 6D:
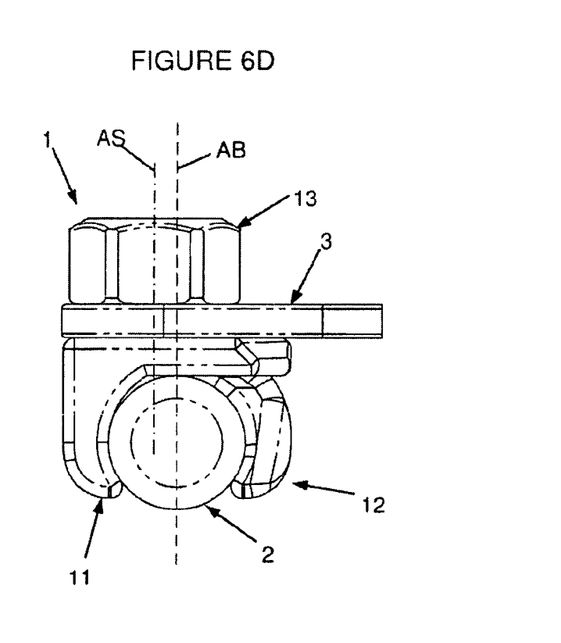

In some embodiments, the fixing head (112) of the first part (11) may be configured to be aligned with the center of the osteosynthesis bar when installed. As particularly shown on FIGS. 6A and 6B, the shape and dimensions of the first part (11) may be, in that case, such that the clamping axis (shown as dotted line AS in FIGS. 6A and 6B) of the clamping resource are aligned to the center of the osteosynthesis bar. In other embodiments, however, the first part (11) may be positioned offset to the osteosynthesis bar (2). As particularly shown on FIGS. 6C and 6D, the shape and dimensions of the first part (11) may be, in that case, such that the clamping axis (AS) is offset from the vertical axis (AB) passing through the center of the osteosynthesis bar (2), for example while still being parallel to this vertical axis (AB). Thus, in such embodiments, the device (1) may be mounted onto the osteosynthesis bar (2) in two different ways. One may choose to offset the clamping resource to the right as shown on FIG. 6C or to offset them to the left as shown on FIG. 6D. Such embodiments may be advantageous to enable, for example, assembling the device (1) with transversal bars (3) of insufficient dimensions with respect to the spacing between two osteosynthesis bars (2), or to enable a fixation of a transversal bar (3) by two devices (1) at two points further apart than devices with a centered vertical axis would enable. Furthermore, such offset embodiments may allow the assembling of the device with different sizes of transverse bars (3). These embodiments thus have an advantage in term of cost for the system composed of the osteosynthesis bars (2), the linking devices (1) and the transversal bars (3), because such devices can be used in systems requiring fewer transversal bars (3) of different sizes, since they may be adapted more easily just by changing the orientation as shown in FIGS. 6C and 6D.

After appreciating this disclosure, it will be apparent to those of skill in the art that this present invention allows embodiments and methods of implementation in many other forms without moving outside the spirit of the invention as claimed. As a consequence, the disclosed embodiments and methods are illustrative only, and may be modified within the scope of attached claims, and the invention is not limited to the details given above.

The invention claimed is:

1. A transverse spinal linking device for attaching a spinal osteosynthesis bar to a transverse bar comprising:
   a clamping resource having a bearing surface configured to bear on the transverse bar when fixing the transverse bar;
   a first part comprising
      a first jaw configured to grip the spinal osteosynthesis bar,
      a fixing head disposed along a vertical axis and configured to mate with the clamping resource such that the clamping resource can descend along the vertical axis, and
      at least one first sliding surface that is inclined in relation to the vertical axis; and
   a second part separate from the first part comprising
      a second jaw configured to grip the spinal osteosynthesis bar,
      a fixing body having a fixing body passage configured to receive the fixing head,
      at least one bearing surface configured to support the transverse bar and such that that the descent of the clamping resource provides for the pressing of the transverse bar against the bearing surface and the fixing of the transverse bar with the transverse spinal linking device, with the pressing of the transverse bar against the bearing surface urging the descent of the second part in relation to the first part, and
      at least one second sliding surface configured to mate with the at least one first sliding surface, with the mating of the first and second sliding surfaces configured such that the descent of the clamping resource provides for
the approach of the first jaw and the second jaw, and
the fixing of the osteosynthesis bar and transverse spinal linking device.

2. A device according to claim 1 in which the first jaw and the second jaw have shapes and dimensions configured to grip the osteosynthesis bar without covering a substantial part of the periphery of the osteosynthesis bar.

3. A device according to claim 1 further comprising at least one stop element configured to limit the approach of the first and second jaws and provide, in the closest approach position of the first and second jaws, sufficient space for placement of the device onto the osteosynthesis bar.

4. A device according to claim 1 in which the first and second jaws are substantially symmetrical and include clamping surfaces configured to act in an opposing manner on the osteosynthesis bar and to grip osteosynthesis bars of different diameters.

5. A device according to claim 1 in which the first part further comprises a surface that is substantially horizontal and flat and configured to mate with a flat area on the osteosynthesis bar.

6. A device according to claim 1 in which the fixing head has a substantially cylindrical shape, and the fixing body passage has a substantially oblong or elongated shape configured to allow transverse play of the second part in relation to the first part and to allow the approach of the first and second jaws.

7. A device according to claim 1 in which the first part further comprises a first part passage that is substantially oblong or elongated along the vertical axis and that is configured to accept the transverse bar and allow its descent along the vertical axis; and the second part further comprises a second part passage that is configured to accept the transverse bar and that includes a bearing surface for the transverse bar.

8. A device according to claim 7 in which the fixing head comprises a vertical conduit that opens onto the first part passage and that is configured to receive the clamping resource.

9. A device according to claim 8 in which the vertical conduit comprises a tapping configured to mate with a thread on the clamping resource.

10. A device according to claim 9 in which the first part passage and the second part passage are oriented to allow fixing of the transverse bar substantially perpendicular to the osteosynthesis bar.

11. A device according to claim 9 in which the shapes and dimensions of the first part passage and the second part passage are configured to allow movement of the transverse bar around at least one axis perpendicular to the osteosynthesis bar.

12. A device according to claim 1 in which the fixing head further comprises a stud configured to project through the fixing body passage, to project through a transverse bar passage of the transverse bar, and to receive the clamping resource, and in which the fixing body passage opens onto the at least one bearing surface.

13. A device according to claim 12 in which the stud comprises a thread configured to mate with a tapping on the clamping resource.

14. A device according to claim 12 in which the bearing surface is substantially flat and configured to mate with a surface of the transverse bar.

15. A spinal stabilization system that comprises at least one transverse bar, at least one osteosynthesis bar, and at least one transverse spinal linking device comprising:
a clamping resource having a bearing surface configured to bear on the transverse bar when fixing the transverse bar;
a first part comprising
a first jaw configured to grip the spinal osteosynthesis bar,
a fixing head disposed along a vertical axis and configured to mate with the clamping resource such that the clamping resource can descend along the vertical axis, and
at least one first sliding surface that is inclined in relation to the vertical axis; and
a second part separate from the first part comprising
a second jaw configured to grip the spinal osteosynthesis bar,
a fixing body having a fixing body passage configured to receive the fixing head,
at least one bearing surface configured to support the transverse bar and such that that the descent of the clamping resource provides for the pressing of the transverse bar against the bearing surface and the fixing of the transverse bar with the transverse spinal linking device, with the pressing of the transverse bar against the bearing surface urging the descent of the second part in relation to the first part, and
at least one second sliding surface configured to mate with the at least one first sliding surface, with the mating of the first and second sliding surfaces configured such that the descent of the clamping resource provides for
the approach of the first jaw and the second jaw, and
the fixing of the osteosynthesis bar and transverse spinal linking device.

16. A spinal stabilization system according to claim 15 in which the fixing head further comprises a stud configured to project through the fixing body passage, to project through a transverse bar passage of the transverse bar, and to receive the clamping resource, and in which the fixing body passage opens onto the at least one bearing surface.

17. A device according to claim 16 in which the stud and the transverse bar passage have shapes and dimensions configured to allow movement of the transverse bar in relation to the device.

18. A spinal stabilization system according to claim 15 in which the first jaw and the second jaw have shapes and dimensions configured to grip the osteosynthesis bar without covering a substantial part of the periphery of the osteosynthesis bar.

19. A spinal stabilization system according to claim 15 in which the first part further comprises a surface that is substantially horizontal and flat and configured to mate with a flat area on the osteosynthesis bar.

20. A spinal stabilization system according to claim 15 in which the fixing head has a substantially cylindrical shape, and the fixing body passage has a substantially oblong or elongated shape configured to allow transverse play of the second part in relation to the first part and to allow the approach of the first and second jaws.

* * * * *